United States Patent [19]
Jousinen et al.

[11] Patent Number: 6,041,928
[45] Date of Patent: Mar. 28, 2000

[54] INNER PACKAGING FOR ABDOMINAL TOWELS STERILE-PACKED IN AN OUTER PACKAGING

[75] Inventors: Erkki Jousinen, Mikkeli, Finland; Lennart Nilsson, Hovås, Sweden; Ulf Johannisson, Landvetter, Sweden; Staffan Kuse, Hindås, Sweden

[73] Assignee: Molnlycke Health Care AB, Gothenburg, Sweden

[21] Appl. No.: 09/068,197

[22] PCT Filed: Nov. 5, 1996

[86] PCT No.: PCT/SE96/01421

§ 371 Date: Jun. 9, 1998

§ 102(e) Date: Jun. 9, 1998

[87] PCT Pub. No.: WO97/17267

PCT Pub. Date: May 15, 1997

[30] Foreign Application Priority Data

Nov. 6, 1995 [SE] Sweden .................................. 9503905

[51] Int. Cl.7 ............................. B65D 85/16; B65D 65/02
[52] U.S. Cl. .......................... 206/440; 206/494; 206/812; 229/87.05; 383/209
[58] Field of Search ..................................... 206/440, 438, 206/441, 812, 494, 210; 229/87.05; 383/207–209, 204; 609/385.1

[56] References Cited

U.S. PATENT DOCUMENTS

| | | | |
|---|---|---|---|
| 2,750,033 | 6/1956 | Pickens | ............... 206/440 X |
| 2,834,459 | 5/1958 | Rickard et al. | . |
| 3,095,088 | 6/1963 | Blaikie et al. | . |
| 3,856,142 | 12/1974 | Vessalo | ............................... 206/438 X |
| 3,973,567 | 8/1976 | Srinivason et al. | .................. 206/440 X |
| 4,648,513 | 3/1987 | Newmon | .................................. 383/204 |
| 4,765,477 | 8/1988 | Froidh et al. | . |
| 4,998,620 | 3/1991 | Taylor | ..................................... 206/440 |
| 5,462,166 | 10/1995 | Minto et al. | . |

FOREIGN PATENT DOCUMENTS

| | | |
|---|---|---|
| 0 182 553 | 5/1986 | European Pat. Off. . |
| 2 273 279 | 6/1994 | United Kingdom . |
| 2 277 914 | 11/1994 | United Kingdom . |

Primary Examiner—Bryon P. Gehman
Attorney, Agent, or Firm—Young & Thompson

[57] ABSTRACT

An inner packaging for sterilized abdominal towels packed in an outer packaging includes an essentially rectangular sheet of material having pairs of mutually opposing first edges and mutually opposing second edges which are folded around a bundle of abdominal towels placed on the sheet such that a first part of the sheet which includes one of the first edges covers a substantial part of the abdominal towels, and a second part of the sheet which includes the second of the first edges covers part of the inwardly folded first part of the sheet, and such that those sections of each edge in the pair of second edges included in the first and the second inwardly folded sheet-parts lie substantially in line with remaining sections of the second edge concerned. The inner packaging is closed solely by two mutually opposing joints which extend substantially parallel with the second edges of the sheet and join together the end-parts of the inwardly folded sheet-parts and the opposing end-parts of that sheet-part which contains those sections of the second edges towards which the folded sections of the second edges are folded.

10 Claims, 2 Drawing Sheets

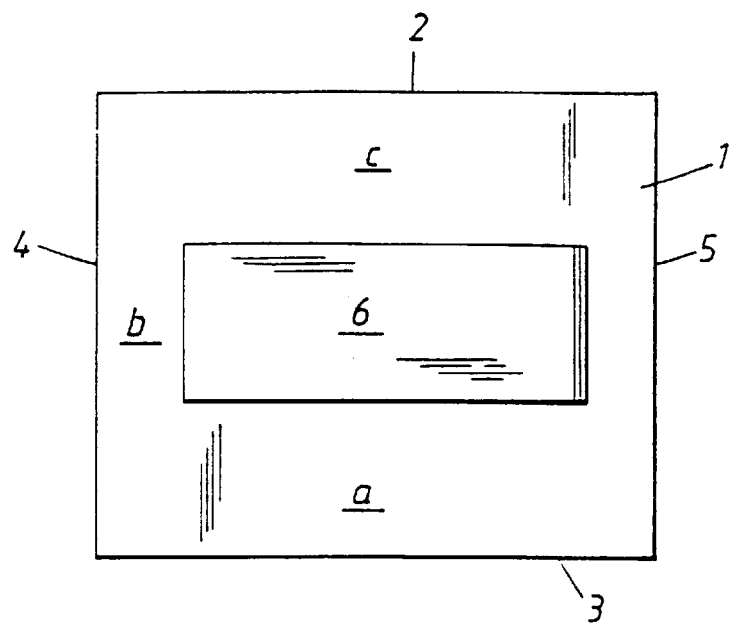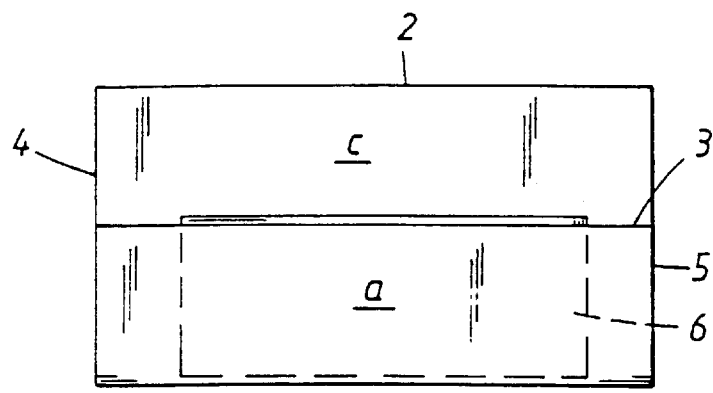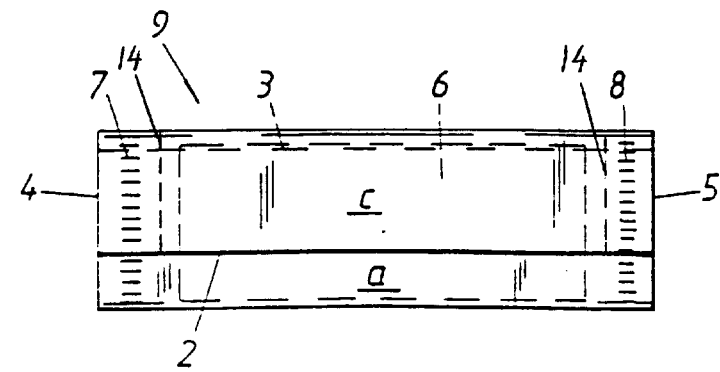

INNER PACKAGING FOR ABDOMINAL TOWELS STERILE-PACKED IN AN OUTER PACKAGING

BACKGROUND OF THE INVENTION

The present invention relates to an inner packaging for abdominal towels sterile-packed in an outer packaging.

Abdominal or surgical towels or surgical compresses are used in surgical operations to dry-up blood and other fluids and to halt the flow of blood in surgical wounds. The abdominal towels are sterile-packed in bundles in an inner packaging which, in turn, is enclosed hermetically in a sterility-maintaining outer packaging. In surgical operations, the outer packaging is opened by a non-sterilized attendant nurse such that a sterilized working nurse is able to remove the inner packaging without touching the non-sterile outer packaging.

Several different types of inner packaging for abdominal towels are known to the art. A first type is comprised of a paper bag which is opened by tearing the bag, and a second type is comprised of composite packaging material comprised of a paper sheet and a plastic sheet that are joined together by a peripheral seam or join while leaving gripping flaps. Both of these packaging types have the drawback of needing two hands to open the packages. A third type is comprised of a paper sheet which is folded in a way to form a closed package by the actual folding procedure. Because of the complicated folding procedure entailed, this type of packaging is not suited for mechanical manufacture and requires a great deal of material in the making. Furthermore, this type of packaging is often difficult to open with one hand.

SUMMARY OF THE INVENTION

The object of the present invention is to provide an easily opened inner packaging for abdominal towels which can be produced easily and cheaply and which is not encumbered with the drawbacks of known inner packagings.

This object is achieved in accordance with the invention by means of an inner packaging for abdominal towels sterile-packed in an outer packaging, characterized in that the inner packaging is comprised of an essentially rectangular sheet of material having pairs of mutually opposing first and second edges which are folded around a bundle of abdominal towels placed on the sheet in a manner such that a first part of the sheet that includes one of the first edges covers a substantial part of the abdominal towels and a second part of the sheet that includes the other of said first edges covers a section of the inwardly folded first sheet part, and such that those sections of each edge in the pair of second edges and included in the first and the second inwardly folded sheet parts lie essentially in line with remaining sections of the second edges concerned; and in that the inner packaging is closed solely by two mutually opposing joins which extend generally parallel with the second edges of the sheet and connect the end-parts of the inwardly folded sheet-parts and the opposing end-parts of that part of the sheet which includes the sections of the second edges folded onto the folded sections of the second edges, the end-parts containing the inwardly sections of the second edges are mutually joined by means of an easily opened fastening. Packaging of this kind can be easily produced mechanically in a cost-effective manner and can also be easily opened with one hand.

In a preferred embodiment, the sheet is made of paper and said fastening being comprised of a mechanical fastening obtained by embossing the edge-parts that include the second edges.

In another variant, the readily opened fastening is a glue joint.

In a second embodiment, at least the inwardly folded second part of the sheet is perforated at its end-parts containing the second edges along lines which extend parallel with the joins and which are further remote from the outer ends of the end-parts than said joins.

BRIEF DESCRIPTION OF THE DRAWINGS

The invention will now be described with reference to the accompanying drawings, in which FIGS. 1–3 illustrate one embodiment of an inventive inner packaging from above and show various steps in the manufacture thereof;

DESCRIPTION OF THE PREFERRED EMBODIMENTS

Figure 4:
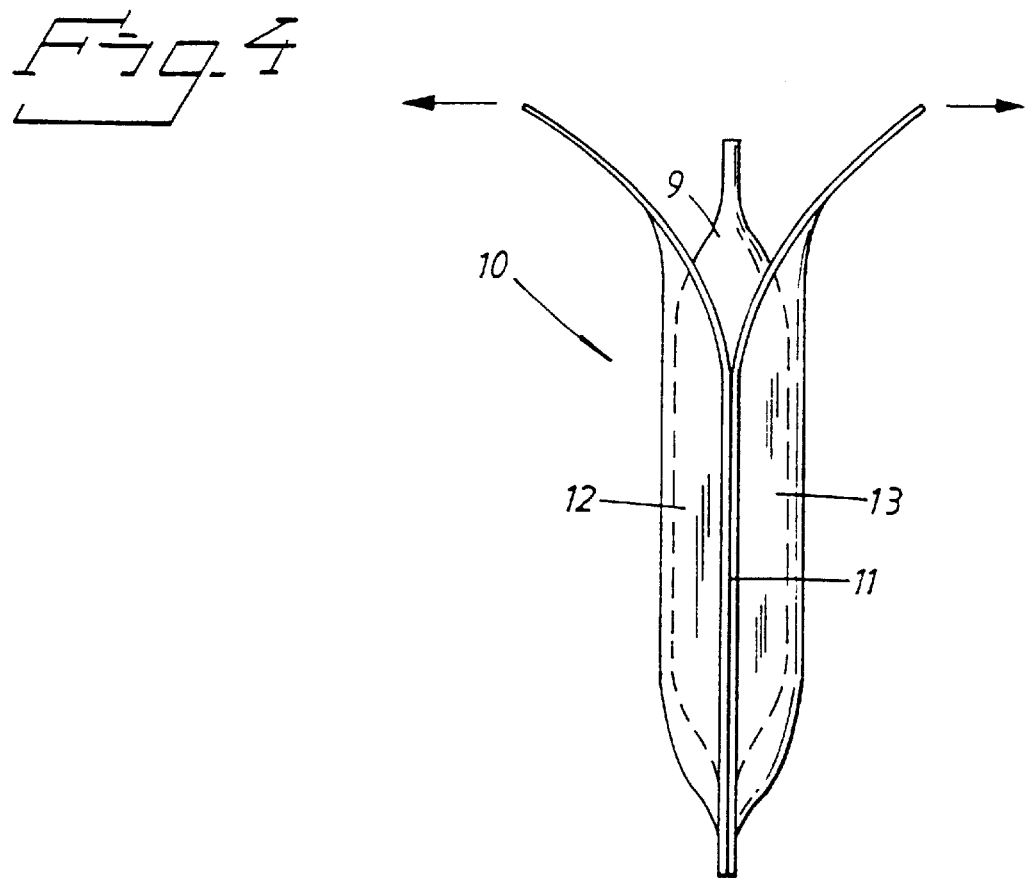
FIG. 4 is a schematic side view of an inner packaging packed in an open outer packaging.

Shown in FIG. 1 is a paper sheet 1 having a first pair of mutually opposing edges 2, 3 and a second pair of mutually opposing edges 4, 5. A bundle 6 of five abdominal towels or surgical compresses, for instance, is placed on the sheet. The bundle 6 divides the sheet 1 into a first and a second part a and c respectively, these parts being located outwardly of the bundle 6 and an extension of its long edges, and an intermediate third part b. An inner packaging is formed in accordance with the invention by folding the first part a of the sheet 1 in over the bundle 6, to obtain the configuration shown in FIG. 2 The part c of the sheet 1 is then folded in over the bundle 6 and the inwardly folded part a. Subsequent to this, the formed inner packaging is closed by joining the end-parts containing the edges 4 and 5 of the inwardly folded parts together and with corresponding end-parts of the sheet part b by means of joins or fastenings 7, 8 which extend generally parallel to the edges 4 and 5. In the illustrated case, the fastenings 7, 8 have the form of a row of grooves embossed in the paper in the same way as the fastenings in coffee filter paper.

FIG. 3 thus shows a finished inner packaging 9 for the bundle of abdominal towels 6. This inner packaging is then placed on a sheet, for instance a paper sheet, whereafter a sheet of weldable material, preferably a plastic material, is placed an top of the inner packaging. These sheets are then joined together with a join that extends peripherally around three edges of the sheets and that is spaced from the fourth edge of said sheet such as to leave gripping flaps which facilitate opening of the outer packaging thus formed. The packaging is then finally sterilized.

FIG. 4 illustrates schematically packaging 10 which includes an outer packaging 11 comprised of a paper sheet 12 and a plastic sheet 13, and an inner packaging 9. In surgical operations, the outer packaging 11 is opened by a non-sterilized attendant nurse, a so-called circulating nurse, by gripping the aforesaid flaps and pulling the packaging apart, as indicated by arrows in FIG. 4, so as to enable the inner packaging 9 to be removed by a sterilized working nurse without coming into contact with the outer surfaces of the outer packaging.

Figure 5:
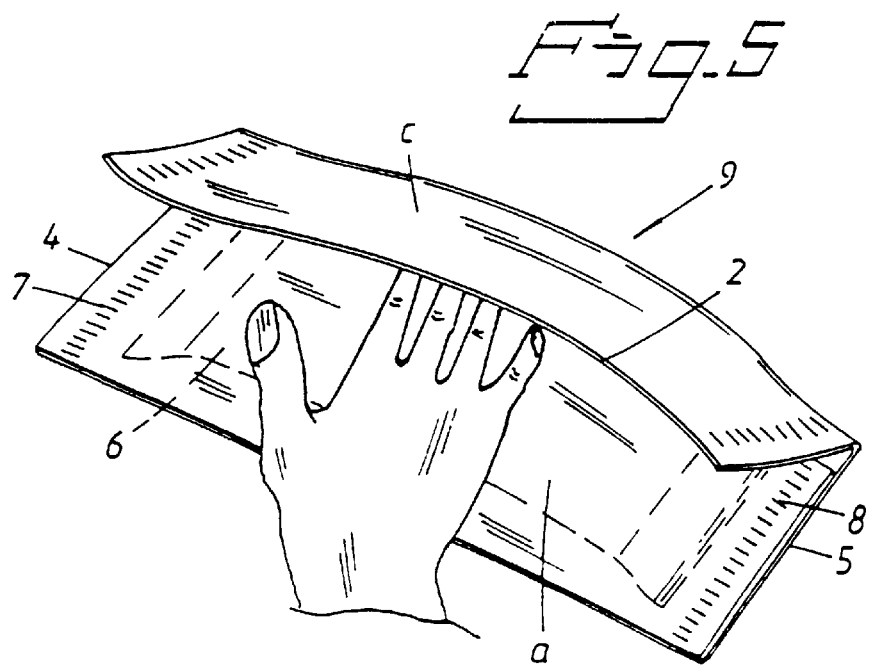
FIG. 5 is a perspective view of a partially open inner packaging.

FIG. 5 shows schematically how an inner packaging 9 can be opened with one hand. Because the part c of the inner packaging is fastened to the remainder of the packaging solely at its end-parts containing the edge 4 and 8, a hand can easily be inserted in between the parts a and c of the inner packaging 9, Thereafter the part c can be lifted up in relation to the part a while breaking the fastening between the parts a, b and c in the end-parts.

Naturally, other types of fastenings than the schematically illustrated joins 7, 8 can be used, for instance other types of mechanical fasteners glue joins, etc., which may be intermittent or continuous. If the sheet material used for forming the inner package is made of a weldable material the joins can of course be made by heat or ultrasonic welding, for instance.

In one variant of the invention, the openability can be achieved with a row of perforations 14 (shown if FIG. 3) or some other type of weakening lines formed in the end-parts, these weakening lines being located inwardly of each join, i.e. further away from the outer ends, and extending parallel with the joins in at least the part c of the packaging.

It will be understood that the described embodiment can be modified within the scope of the invention. For instance, the inner packaging may be comprised of other sheet material than paper, for instance plastic material. The parts a and c of the sheet 1 may have other dimensions than those shown in FIGS. 1–3, for instance the part a may be smaller, such that the edge 2 in the inwardly folded position of the part a will lie further away from the long edge of the bundle 6 than in the case of the embodiment shown in FIG. 2. The bundle 6 may, of course, comprise more than or fewer than five abdominal towels. Furthermore, the inwardly folded parts of the inner packaging may be joined together in stages, for instance the parts a and b folded inwardly towards one another may be joined together in conjunction with folding the part a in towards the part b to the position shown in FIG. 2. The invention is therefore solely limited by the contents of the following claims.

We claim:

1. Inner packaging (9) for sterilized abdominal towels (6) packed in an outer packaging (11), wherein the inner packaging (9) comprises a substantially rectangular sheet of material (1) having pairs of mutually opposing first edges (2, 3) and mutually opposing second edges (4, 5), which are folded around a bundle (6) of abdominal towels placed on the sheet such that a first part (a) of the sheet which includes one (3) of the first edges (2, 3) covers a substantial part of the abdominal towels, and a second part (c) of the sheet which includes the second (2) of said first edges (2, 3) covers part of the inwardly folded first part (a) of the sheet, and such that those sections of each edge (4, 5) in the pair of second edges included in the first and the second inwardly folded sheet-parts (a, c) lie substantially in line with remaining sections of the second edge concerned;

wherein the inner packaging (9) is closed solely by two mutually opposing easily opened fastenings (7, 8) which extend substantially parallel with the second edges (4, 5) of said sheet and join the inwardly folded sheet-parts (a, c) and opposing end-parts of an intermediate sheet-part (b) directly to each other, said intermediate sheet-part contains those sections of the second edges (4, 5) towards which the folded sections of the second edges are folded.

2. The inner packaging according to claim 1, wherein the sheet (1) is a paper sheet and the easily opened fastenings (7, 8) are mechanical fastenings produced by embossing the edge-parts that contain the second edges (4, 5).

3. The inner packaging according to claim 1, wherein the easily opened fastenings are glue joins.

4. The inner packaging according to claim 1, wherein at least the inwardly folded second part of the sheet is perforated adjacent to the second edges along lines which are parrallel with the easily opened fastenings and that are further from the second edges than the easily opened fastenings.

5. A package comprising an inner package in and outer package, said inner package comprising a substantially rectangular sheet and a sterile bundle having a bottom surface on said sheet, said sheet having first and second opposing edges and third and fourth opposing edges, wherein said first edge is folded onto a top surface of said sterile bundle opposite said bottom surface and said second edge is folded onto said top surface of said bundle and covering said first edge so that distal portions of said third edge overlap one another and distal portions of said fourth edge overlap one another, wherein said inner package is closed solely with first and second fastenings that are generally parallel to said third and fourth edges and that join overlappings portions of said sheet adjacent said third edge and said fourth edge, respectively, and wherein a portion of said sheet on said top surface of said bundle is perforated along lines that are generally parallel to said third and fourth edges and that are each separated from said third and fourth edges by a respective one of said first and second fastenings.

6. The package of claim 5, wherein said first and second fastenings are glue joins.

7. The package of claim 5, wherein said first and second fastenings are grooves embossed in said sheet.

8. The package of claim 5, wherein said sheet comprises paper.

9. The package of claim 5, wherein said bundle comprises one of plural towels and plural compresses.

10. The package of claim 5, wherein said outer package comprises a further four-edged sheet and a plastic four-edged sheet that are joined at only three of their four edges, whereby said inner package is accessible through the open one of the four edges.

* * * * *